US010011653B2

(12) United States Patent
Hayashi et al.

(10) Patent No.: US 10,011,653 B2
(45) Date of Patent: Jul. 3, 2018

(54) ANTIBODIES TO TAU AND METHODS OF TREATMENT THEREWITH

(71) Applicant: Eli Lilly and Company, Indianapolis, IN (US)

(72) Inventors: Mansuo Lu Hayashi, Carmel, IN (US); Jirong Lu, Carmel, IN (US); David Driver, Solana Beach, CA (US); Alberto Alvarado, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/347,883

(22) Filed: Nov. 10, 2016

(65) Prior Publication Data

US 2017/0107278 A1 Apr. 20, 2017

Related U.S. Application Data

(63) Continuation of application No. 15/046,668, filed on Feb. 18, 2016, now Pat. No. 9,527,909.

(60) Provisional application No. 62/121,116, filed on Feb. 26, 2015.

(51) Int. Cl.
G01N 33/53 (2006.01)
A61K 39/395 (2006.01)
A61K 39/00 (2006.01)
C07K 16/18 (2006.01)

(52) U.S. Cl.
CPC ........ C07K 16/18 (2013.01); A61K 2039/505 (2013.01); C07K 2317/24 (2013.01); C07K 2317/52 (2013.01); C07K 2317/565 (2013.01); C07K 2317/567 (2013.01); C07K 2317/76 (2013.01); C07K 2317/92 (2013.01); C07K 2317/94 (2013.01)

(58) Field of Classification Search
CPC .......................... C07K 16/18; C07K 2317/34; C07K 2317/76; C07K 14/4711; C07K 2317/565; C07K 2317/56; C07K 2317/55; C07K 16/461; C07K 2317/21; C07K 2317/567; C07K 16/00; G01N 33/6896; G01N 2800/2821; G01N 2333/4709; G01N 2800/28; G01N 2800/2814; G01N 33/5058; A61K 2039/505; A61K 2300/00; A61K 39/3955; A61K 39/0007; A61K 47/48538; A61K 2039/53; A61K 39/395; Y01S 424/80; A01K 2267/03
See application file for complete search history.

(56) References Cited

U.S. PATENT DOCUMENTS

| | | |
|---|---|---|
| 5,811,310 A | 9/1998 | Ghanbari et al. |
| 7,161,060 B1 | 1/2007 | Duff et al. |
| 7,238,788 B2 | 7/2007 | Lee |
| 7,442,516 B2 | 10/2008 | Ohno et al. |
| 7,446,180 B2 | 11/2008 | Novak |
| 8,012,936 B2 | 9/2011 | Sigurdsson et al. |
| 8,609,097 B2 | 12/2013 | Bohrmann et al. |
| 8,647,631 B2 | 2/2014 | Pfeifer et al. |
| 8,697,076 B2 | 4/2014 | Binder et al. |
| 8,703,137 B2 | 4/2014 | Chain |
| 8,771,693 B2 | 7/2014 | Lu et al. |
| 8,778,343 B2 | 7/2014 | Kayed |
| 8,926,974 B2 | 1/2015 | Griswold-Prenner et al. |
| 8,940,272 B2 | 1/2015 | Nitsch et al. |
| 8,980,270 B2 | 3/2015 | Griswold-Prenner et al. |
| 8,980,271 B2 | 3/2015 | Griswold-Prenner et al. |
| 9,051,367 B2 | 6/2015 | Griswold-Prenner et al. |
| 9,139,643 B2 | 9/2015 | Sigurdsson et al. |
| 9,290,567 B2 | 3/2016 | Bohrmann et al. |
| 9,304,138 B2 | 4/2016 | Pfeifer et al. |
| 2007/0218491 A1 | 9/2007 | Vasan et al. |
| 2008/0220449 A1 | 9/2008 | Vasan et al. |
| 2012/0244174 A1 | 9/2012 | Chain |
| 2013/0095492 A1 | 4/2013 | DeBernardis et al. |
| 2013/0295021 A1 | 11/2013 | Chen et al. |
| 2014/0056901 A1 | 2/2014 | Agadjanyan et al. |
| 2014/0099303 A1 | 4/2014 | Griswold-Prenner et al. |
| 2014/0099304 A1 | 4/2014 | Griswold-Prenner et al. |
| 2014/0161875 A1 | 6/2014 | Winderickx et al. |
| 2014/0255412 A1 | 9/2014 | Pfeifer et al. |
| 2014/0294731 A1 | 10/2014 | Pfeifer et al. |
| 2014/0294839 A1 | 10/2014 | Kuret et al. |
| 2014/0302046 A1 | 10/2014 | Sigurdsson |
| 2015/0004169 A1 | 1/2015 | Kayed |
| 2015/0175682 A1 | 6/2015 | Pfeifer et al. |
| 2015/0239963 A1 | 8/2015 | Griswold-Prenner et al. |

(Continued)

FOREIGN PATENT DOCUMENTS

| | | |
|---|---|---|
| EP | 0279454 A2 | 8/1988 |
| WO | 2004016655 A1 | 2/2004 |
| WO | 2005080986 A1 | 9/2005 |

(Continued)

OTHER PUBLICATIONS

Harper Biochimica et Biophysica Acta 2010; 1802:785-795.*
Tayebati. Mech. Ageing Dev. 2006. 127: 100-8.*
Sarter. Neurosci. and Biobehav. Rev. 2004. 28: 645-650.*
Anger. Neurotoxicology 1991. 12: 403-13.*
Esteves-Villanueva, J.O. et al., Biochemistry (2015) 20;54(2):293-302.
Shahim P. et al., (2014) JAMA Neurology. 71:684-692.
Asuni A., et al., J. of Neuroscience (2007) 27(34): 9115-9129.
Ahmed, Z et al., (2014) Acta Neuropathol. 27(5): 667-683.
Braak, H. et al., Acta Neuropathol (1991) 82:239-259.
Billingsley M. et al., Journal of Biochem. (1997) 323: 577-591.
Boutajangout, A. et al., Journal of Neurochem. (2011) 118: 658-667.
Carmel, G., et al., J. Biol. Chem (1996) 271:32789-32795.
Castillo-Carranza, D., et al., J. of Neuroscience (2014) 34 (12):4260-4272.

(Continued)

Primary Examiner — Chang-Yu Wang
(74) Attorney, Agent, or Firm — Duane Christopher Marks

(57) ABSTRACT

Monoclonal antibodies to human tau aggregate, compositions comprising such tau antibodies, and methods of using such tau antibodies for the treatment of neurodegenerative diseases including Alzheimer's disease, Progressive Supranuclear Palsy and Pick's disease.

6 Claims, No Drawings

(56) References Cited

U.S. PATENT DOCUMENTS

| | | |
|---|---|---|
| 2015/0252102 A1 | 9/2015 | Nitsch et al. |
| 2015/0259406 A1 | 9/2015 | Pfeifer et al. |

FOREIGN PATENT DOCUMENTS

| | | |
|---|---|---|
| WO | 2010142423 A1 | 1/2010 |
| WO | 2010115483 A2 | 10/2010 |
| WO | 2010144711 A2 | 12/2010 |
| WO | 2011026031 A1 | 3/2011 |
| WO | 2012045882 A2 | 4/2012 |
| WO | 2012049570 A1 | 4/2012 |
| WO | 2012106363 A2 | 8/2012 |
| WO | 2013007839 A1 | 1/2013 |
| WO | 2013041962 A1 | 3/2013 |
| WO | 2013050567 A1 | 4/2013 |
| WO | 2013059786 A1 | 4/2013 |
| WO | 2013096380 A2 | 6/2013 |
| WO | 2013151762 A1 | 10/2013 |
| WO | 2014008404 A1 | 1/2014 |
| WO | 2014016737 A1 | 1/2014 |
| WO | 2014028777 A2 | 2/2014 |
| WO | 2014031697 A2 | 2/2014 |
| WO | 2014059442 A2 | 4/2014 |
| WO | 2014096321 A1 | 6/2014 |
| WO | 2014100600 A2 | 6/2014 |
| WO | 2014165271 A2 | 10/2014 |
| WO | 2014200921 A1 | 12/2014 |

OTHER PUBLICATIONS

Chai X., et al. (2011) J Biol Chem. 30:286(39):34457-67.
Clavaguera, et al. (2009) Nature Cell Biol. 11, 909-913.
Collin, L., et al., Brain (2014) 137: 2834-2846.
Clavaguera, F. et al., (2014) Acta Neuropathol. 127: 299-301.
Clavaguera, F. et al., PNAS (2013), vol. 110, No. 23, 9535-9540 F. et al., PNAS (2013), vol. 110, No. 23, 9535-9540.
Frost, B., et al., J. of Biological Chemistry (2009) 284, No. 19, 12845-12852.
Falcon, B et al., (2015) J Biol Chem. 290(2)1049-.
Goedert, M. et al., Trends in Neurosciences (2010) 33: 317-325.
Goedert, M. et al., Neuron (1989) 3: 519-526.
Gotz, J. et al., Biochimica et Biophysica Acta (2010) 1802: 860-871.
Gu J., et al., J. of Biol. Chem. (2013) 288:33081-33095.
Golde, T. et al., Neuron (2013) 80:254-256.
Guo J., et al., J. of Biol. Chem. (2011) 286(17):15317-15331.
Gerson, J., et al. Frontiers in Neurology (2013) vol. 4, Art.93, 1-10.
Haroutunian, V., et al., Neurobiol. of Aging (2007) 28:1-7.
Hyman, B. et al., (2012) Alzheimers Dement. 2012;8(1):1-13.
Ittner, A., et al., J. of Neurochem. (2015), 10.1111/jnc.12821.
Jicha, G. et al., J. Neurosci. Res. (1999), 55: 713-723.
Jicha, G. et al., (1997) J. Neurosci. Res., 48(2), 128-132.
Jicha, G. et al., J. Neurochem (1997) 69(5): 2087-2095.
Koerber, J. et al., Nature Biotechnology (2013) 31(10) 916-923.
Kfoury, N. et al., J Biol Chem. (2012) 287, No. 23, 19440-19451.
Kontsekova, E. et al., Alzheimer's Research & Therapy (2014) 6:45.
Liu, L. et al., www.plosone.org, (2012) vol. 7, Issue 2, e31302.
Lewis J. et al., (2000) Nat Genet. 25:402-405.
Lichrenberg-Kraag, B. et al., Biochem. (1992) 89:5384-5388.
Nakamura, K. et al., Cell (2012), 149: 232-244.
Otvos, L., et al., J. Neuroscience Res. (1994) 39:669-673.
Polydoro, M. et al., J. or Neuroscience (2013) 33(33): 13300-13311.
Pooler, A. et al., J. of Comparative Neurology (2013), 521: 4236-4248.
Ramsden, M., et al., (2005) J. Neuroscience. 25: 10637-10647.
Santa-Maria, I. et al., J Biol Chem. (2012) 287, No. 24, 20522-20533.
Saper, C.B. et al., Neuroscience (1987) vol. 23, No. 2, 389-398.
Sanders, D. et al., Neuron (2014), 82:1271-1288.
Santacruz K., et al., (2005) Science. 309(5733):476-81.
Selkoe, D. et al., (1991) Neuron. 6(4):487-498.
Uboga, N.V., et al., Neurobiol. of Aging (2000) 21:1-10.
Weaver, C., et al., Neurobiol. of Aging (2000) 21:719-727.
Wu J. et al., J Biol Chem. (2013) 288, No. 3, 1856-1870.
Wolozin, B. et al., Science (1986) 232:648-650.
Yanamandra, K. et al., Annals of Clin. and Translational Neurology (2015) 2(3): 278-288.
Yanamandra,, K. et al., Neuron (2013) 80:402-414.
51. Zetterberg H. et al., (2013) Alzheimers Res Ther. 5(2):9.

* cited by examiner

ANTIBODIES TO TAU AND METHODS OF TREATMENT THEREWITH

The present invention is in the field of medicine. Particularly, the present invention relates to antibodies to tau, compositions comprising such tau antibodies, and methods of using such tau antibodies for the treatment of neurodegenerative diseases including Alzheimer's Disease (AD), Progressive Supranuclear Palsy (PSP), and Pick's Disease (PD).

Tau is an axonal microtubule binding protein that promotes microtubule assembly and stability. AD and PSP are neurodegenerative diseases pathologically characterized by aberrant tau aggregation. More specifically, in AD and PSP, hyperphosphorylated tau is believed to promote insoluble tau fibril aggregation leading to microtubule destabilization, and neuronal toxicity. Cell culture and murine model studies have shown tau aggregates spread across neuronal synapse junctions and sequester monomeric (native or non-aggregated) tau, inducing tau aggregate formation. Neuroanatomical progression of tau aggregation and accumulation in neurodegenerative diseases such as AD and PSP suggests that tau fibril aggregation propagates along neuronal networks, ultimately resulting in destabilization of microtubules and ultimately localized impaired neuronal function.

The density and neuroanatomical localization of tau aggregation correlates strongly with AD and PSP neurologic symptoms and disease progression. For example, in AD, tau forms intraneuronal neurofibrillary tangles (NFTs), which tend to develop in sequence from transentorhinal, to limbic, to neocortical regions, and which correlate with severity of dementia and extent of neuronal loss. In PSP, tau aggregation is seen in neurons, astrocytes, and oligodendrocytes within subcortical and cortical regions, and the density of aggregated tau has been shown to correlate with the severity of neuronal loss.

Antibodies to tau are known. For example, U.S. Pat. No. 8,926,974, and International Publication Nos. WO2011/026031, WO2012/049570, and WO2013/050567 disclose antibodies to tau and uses of tau antibodies for the treatment of neurodegenerative diseases such as AD. However, to date no antibody targeting tau has been approved for therapeutic use and there are currently no approved disease modifying therapies for AD or PSP. Thus, there remains a need for alternative tau antibodies. In particular, there remains a need for alternative tau antibodies which specifically bind tau aggregates and which reduce the propagation of tau aggregate formation, NFT formation and neuronal loss. Such tau antibodies preferably also possess good physical-chemical properties to facilitate development, manufacturing, and/or formulation.

The present invention provides a monoclonal antibody that binds human tau and which comprises a light chain variable region (LCVR) and a heavy chain variable region (HCVR), wherein the LCVR comprises complementarity determining regions (CDRs) LCDR1, LCDR2 and LCDR3 and the HCVR comprises CDRs HCDR1, HCDR2 and HCDR3. According to particular embodiments of the present invention the amino acid sequence of LCDR1 is given by SEQ ID NO. 3, the amino acid sequence of LCDR2 is given by SEQ ID NO. 4, the amino acid sequence of LCDR3 is given by SEQ ID NO. 5, the amino acid sequence of HCDR1 is given by SEQ ID NO. 6, the amino acid sequence of HCDR2 is given by SEQ ID NO. 7, and the amino acid sequence of HCDR3 is given by SEQ ID NO. 8. In an embodiment, the present invention provides a monoclonal antibody that binds human tau, comprising a LCVR and a HCVR, wherein the amino acid sequence of the LCVR is given by SEQ ID NO. 9 and the amino acid sequence of the HCVR is given by SEQ ID NO. 10. In a further embodiment, the present invention provides a monoclonal antibody that binds human tau, comprising a light chain (LC) and a heavy chain (HC), wherein the amino acid sequence of the LC is given by SEQ ID NO. 1 and the amino acid sequence of the HC is given by SEQ ID NO. 2.

The present invention provides a monoclonal antibody that binds human tau. In an embodiment, the present invention provides a monoclonal antibody that binds a conformational epitope of human tau. In a particular embodiment, the conformational epitope of human tau includes amino acid residues 7-9 and 312-322 of human tau, wherein the amino acid sequence of the human tau is given by SEQ ID NO. 13.

The present invention further provides pharmaceutical compositions comprising a monoclonal antibody of the present invention and one or more pharmaceutically acceptable carriers, diluents or excipients. Further, the present invention provides a method of treating AD, PSP, or PD comprising administering to a patient in need thereof a pharmaceutical composition of the present invention.

In addition, the present invention provides a method of treating neurodegenerative diseases. More particularly, the present invention provides a method of treating AD, PSP, or PD comprising administering to a patient in need thereof an effective amount of a monoclonal antibody of the present invention.

The present invention also provides the monoclonal antibody of the present invention for use in therapy. More particularly, the present invention also provides the monoclonal antibody of the present invention for use in treatment of AD, PSP, or PD.

In an embodiment, the present invention provides the use of the monoclonal antibody of the present invention in the manufacture of a medicament for the treatment of AD, PSP, or PD.

The present invention also relates to nucleic acid molecules and expression vectors encoding the monoclonal antibody of the present invention. In an embodiment, the present invention provides a DNA molecule comprising a polynucleotide sequence encoding a polypeptide having the amino acid sequence of SEQ ID NO. 1. In an embodiment, the present invention provides a DNA molecule comprising a polynucleotide sequence encoding a polypeptide having the amino acid sequence of SEQ ID NO. 2. In a further embodiment, the present invention provides a DNA molecule comprising a polynucleotide sequence encoding a polypeptide having the amino acid sequence of SEQ ID NO. 1, and comprising a polynucleotide sequence encoding a polypeptide having the amino acid sequence of SEQ ID NO. 2. In a particular embodiment the polynucleotide sequence encoding a polypeptide having the amino acid sequence of SEQ ID NO. 1 is given by SEQ ID NO. 11 and the polynucleotide sequence encoding a polypeptide having the amino acid sequence of SEQ ID NO. 2 is given by SEQ ID NO. 12.

Further, the present invention provides a monoclonal antibody prepared according to a process, wherein said process comprises cultivating a host cell comprising a polynucleotide sequence encoding a polypeptide having the amino acid sequence of SEQ ID NO. 1 and a polynucleotide sequence encoding a polypeptide having the amino acid sequence of SEQ ID NO. 2, under conditions such that the monoclonal antibody is expressed, and recovering from said host cell a monoclonal antibody comprising a LC and a HC, wherein the amino acid sequence of the LC is given by SEQ ID NO. 1 and the amino acid sequence of the HC is given by SEQ ID NO. 2.

As used herein, an "antibody" is an immunoglobulin molecule comprising 2 HCs and 2 LCs interconnected by disulfide bonds. The amino terminal portion of each LC and HC includes a variable region of about 100-120 amino acids primarily responsible for antigen recognition via the CDRs contained therein. The CDRs are interspersed with regions that are more conserved, termed framework regions ("FR"). Each LCVR and HCVR is composed of 3 CDRs and 4 FRs, arranged from amino-terminus to carboxy-terminus in the following order: FR1, CDR1, FR2, CDR2, FR3, CDR3, FR4. The 3 CDRs of the LC are referred to as "LCDR1, LCDR2, and LCDR3," and the 3 CDRs of the HC are referred to as "HCDR1, HCDR2, and HCDR3." The CDRs contain most of the residues which form specific interactions with the antigen. The functional ability of an antibody to bind a particular antigen is largely influenced by the six CDRs. Assignment of amino acids to CDR domains within the LCVR and HCVR regions of the antibodies of the present invention is based on the well-known Kabat numbering convention (Kabat, et al., *Ann. NY Acad. Sci.* 190: 382-93 (1971); Kabat et al., *Sequences of Proteins of Immunological Interest*, Fifth Edition, U.S. Department of Health and Human Services, NIH Publication No. 91-3242 (1991)), and North numbering convention (North et al., *A New Clustering of Antibody CDR Loop Conformations*, Journal of Molecular Biology, 406:228-256 (2011)).

LCs are classified as kappa or lambda, which are each characterized by a particular constant region as known in the art. The monoclonal antibodies of the present invention include kappa LCs. HCs are classified as gamma, mu, alpha, delta, or epsilon, and define the isotype of an antibody as IgG, IgM, IgA, IgD, or IgE, respectively. The monoclonal antibodies of the present invention include IgG HCs. IgG antibodies can be further divided into subclasses, e.g., IgG1, IgG2, IgG3, IgG4. In a particular embodiment, the monoclonal antibodies of the present invention are IgG4. The carboxy-terminal portion of each HC defines a constant region primarily responsible for effector function. In a particular embodiment, the monoclonal antibodies of the present invention have one or more modifications in the constant region of each HC that reduces effector function. In a more particular embodiment, the monoclonal antibodies of the present invention are IgG4 and have modifications in the constant region of both HCs that reduce effector function including the amino acid alanine at both residues 230 and 231 (residue numbering based on the exemplified HC of SEQ ID NO. 2). In an even more particular embodiment, the monoclonal antibodies of the present invention are IgG4 and have modifications in the constant region of both HCs that reduce effector function including the amino acid alanine at both residues 230 and 231 and have further modifications in the constant region of both HCs promoting stability including the amino acid proline at residue 224 and the deletion of the amino acid lysine at residue 443 (residue numbering based on the exemplified HC of SEQ ID NO. 2).

The antibodies of the present invention are monoclonal antibodies ("mAbs"). The mAbs for the present invention are complete mAbs containing 2 HCs and 2 LCs. As referred to herein, mAbs are antibodies derived from a single copy or clone including, for example, any eukaryotic, prokaryotic or phage clone, and not the method by which it is produced. Monoclonal antibodies can be produced, for example, by hybridoma technologies, recombinant technologies, phage display technologies, synthetic technologies, e.g., CDR-grafting, or combinations of such or other technologies known in the art.

Methods of producing and purifying antibodies are well known in the art and can be found, for example, in Harlow and Lane (1988), *Antibodies, A Laboratory Manual*, Cold Spring Harbor Laboratory Press, Cold Spring harbor, N.Y., chapters 5-8 and 15, ISBN 0-87969-314-2. For example, mice can be immunized with human tau paired helical filaments ("PHF") from brain tissue of patients characterized as having AD (Jicha et al., J. Neurosci. Res., 15:48(2), 128-132 (April, 1997)), and the resulting antibodies can be recovered, purified, and the amino acid sequences determined using conventional methods well known in the art. The monoclonal antibodies of the present invention are engineered to contain one or more human framework regions surrounding CDRs derived from a non-human antibody. Human framework germline sequences can be obtained from ImMunoGeneTics (INGT) via their website, http://imgt.cines.fr, or from *The Immunoglobulin FactsBook* by Marie-Paule Lefranc and Gerard Lefranc, Academic Press, 2001, ISBN 012441351. According to particular embodiments of the present invention, particular germline HC framework and LC framework regions for use in monoclonal antibodies of the present invention include 5-51 and A27, respectively.

In particular embodiments of the present invention, the antibody, or the nucleic acid encoding same, is provided in isolated form. As used herein, the term "isolated" refers to a protein, peptide, or nucleic acid which is free or substantially free from other macromolecular species found in a cellular environment.

The monoclonal antibodies of the present invention may be prepared and purified using known methods. For example, cDNA sequences encoding a HC (for example the amino acid sequence given by SEQ ID NO. 2) and a LC (for example, the amino acid sequence given by SEQ ID NO. 1) may be cloned and engineered into a GS (glutamine synthetase) expression vector. The engineered immunoglobulin expression vector may then be stably transfected into CHO cells. As one of skill in the art will appreciate, mammalian expression of antibodies will result in glycosylation, typically at highly conserved N-glycosylation sites in the Fc region. Stable clones may be verified for expression of an antibody specifically binding to tau aggregates. Positive clones may be expanded into serum-free culture medium for antibody production in bioreactors. Media, into which an antibody has been secreted, may be purified by conventional techniques. For example, the medium may be conveniently applied to a Protein A or G Sepharose FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and then pooled. The antibody may be concentrated and/or sterile filtered using common techniques. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

The monoclonal antibodies of the present invention can be used in the treatment of patients. More particularly the antibodies of the present invention are expected to treat a class of neurodegenerative disorders, termed tauopathies, which includes AD, PSP, and PD. Although monoclonal antibodies of the present invention are expected to be useful in the treatment of AD, PSP, and PD, such antibodies may also be useful in the treatment of other tauopathies, including chronic traumatic encephalopathy. As used interchangeably herein, "treatment" and/or "treating" and/or "treat" are intended to refer to all processes wherein there may be a slowing, interrupting, arresting, controlling, stopping, or reversing of the progression of the disorders described herein, but does not necessarily indicate a total elimination of all disorder symptoms. Treatment includes administration of an antibody of the present invention for treatment of a disease or condition in a human that would benefit from a reduction in the propagation of at least one of tau aggregate formation, NFT formation and neuronal loss, and includes: (a) inhibiting further progression of the disease, i.e., arresting its development; and (b) relieving the disease, i.e., causing regression of the disease or disorder or alleviating symptoms or complications thereof.

As used interchangeably herein, the term "patient," "subject," and "individual," refers to a human. In certain embodiments, the patient is further characterized with a disease, disorder, or condition (e.g., a neurodegenerative disorder) that would benefit from a reduction in the propagation of at least one of tau aggregate formation, NFT formation, and neuronal loss. In another embodiment, the patient is further characterized as being at risk of developing a neurodegenerative disorder, disease, or condition that would benefit from a reduction in the propagation of at least one of tau aggregate formation, NFT formation, and neuronal loss.

As used herein, the term "bind (or binds)" tau refers to an interaction of an antibody with an epitope of human tau aggregate. More preferably, the epitope is a conformational epitope of human tau. In a particular embodiment, the term "bind (or binds)" tau refers to an interaction with a conformational epitope including amino acid residues 7-9 and 312-322 of human tau aggregate (residue numbering based on the exemplified human tau of SEQ ID NO. 13). It should be understood that there are known variations of human tau protein, for example resulting from splice variants. Such known variations, however, possess the conformational epitope including amino acid residues 7-9 and 312-322 of SEQ ID NO. 13. Known variants, however, may result in altered residue numbering for amino acid residues 7-9 and 312-322 of SEQ ID NO. 13. Although the residue numbering may be altered in some variants, the amino acids comprising the epitope remain the same. The term "epitope" as used herein refers to discrete, three-dimensional sites of an antigen that are recognized by the monoclonal antibodies of the present invention.

A monoclonal antibody of the present invention can be incorporated into a pharmaceutical composition which can be prepared by methods well known in the art and comprise a monoclonal antibody of the present invention and one or more pharmaceutically acceptable carrier(s) and/or diluent(s) (e.g., *Remington, The Science and Practice of Pharmacy*, 22$^{nd}$ Edition, Loyd V., Ed., Pharmaceutical Press, 2012, which provides a compendium of formulation techniques as are generally known to practitioners). Suitable carriers for pharmaceutical compositions include any material which, when combined with the monoclonal antibody of the present invention, retains the molecule's activity and is non-reactive with the patient's immune system.

A pharmaceutical composition comprising a monoclonal antibody of the present invention can be administered to a patient at risk for, or exhibiting, diseases or disorders as described herein by parental routes (e.g., subcutaneous, intravenous, intraperitoneal, intramuscular, or transdermal).

A pharmaceutical composition of the present invention contains an "effective" or "therapeutically effective" amount, as used interchangeably herein, of a monoclonal antibody of the present invention. An effective amount refers to an amount necessary (at dosages and for periods of time and for the means of administration) to achieve the desired therapeutic result. An effective amount of the monoclonal antibody may vary according to factors such as the disease state, age, sex, and weight of the individual, and the ability of the monoclonal antibody to elicit a desired response in the individual. An effective amount is also one in which any toxic or detrimental effects of the monoclonal antibody of the present invention are outweighed by the therapeutically beneficial effects.

Engineered Tau Antibody

Significant problems associated with chemical and physical stability were encountered when constructing a monoclonal tau antibody of the present invention. Problems encountered included low binding affinity, immunogenicity, aggregation, HC dimerization, as well as variable region deamidation, oxidation, isomerization and misfolding.

For example, murine IgG1 antibody MC-1 ("MC-1") (Albert Einstein College of Medicine, Jicha et al., 1997), which recognizes a conformational epitope of tau protein at amino acid residues 7-9 and 312-322 (residue numbering based on exemplified human tau protein having the amino acid sequence of SEQ ID NO. 13), was initially humanized by engineering the three MC-1 murine HC CDRs into multiple human HC framework germline genes and the three MC-1 murine LC CDRs into multiple human LC framework germline genes. Humanized constructs of MC-1 utilized 96 different combinations of heavy- and light-chain frameworks, representing each of the twelve HC framework germline families (specific human HC frameworks: 1-24, 1-46, 1-69, 2-05, 3-15, 3-23, 3-53, 3-72, 4-04, 4-39, 5-51, and 6-01) and each of the eight LC germline families (specific human LC frameworks: A-26, A-27, B-2, B-3, L-2, L-12, O11, and O-2). The respective framework germline genes were cloned into heavy and light chain human IgG4 expression vectors and transfected into HEK293 cells for expression and analysis of binding by ELISA. Although multiple framework pairs demonstrated some level of binding to human tau in ELISA, resulting antibody constructs displayed a myriad of issues including poor binding affinity, aggregation, HC dimerization, and chemical stability issues such as deamidation, oxidation, and isomerization in the variable regions.

Modifications were therefore engineered to develop tau antibodies possessing improved binding affinity, eliminated or reduced HC dimerization, reduced immunogenicity, and improved chemical and physical stability. Amino acid modifications (relative to MC-1, Jicha et al., 1997) were engineered in HCDR2 and HCDR3, and LCDR1, LCDR2, and LCDR3. The modified murine antibody was humanized by engineering the three HC CDRs into multiple human HC framework germline genes and the three LC CDRs into multiple human LC framework germline genes essentially as described above. Further, extensive protein stability studies were performed and the engineered monoclonal antibodies were screened for expression and thermostability properties as well as binding affinity properties. A monoclonal antibody containing seven CDR mutations (amino acid position is based on linear amino acid residue numbering of an exemplified antibody of the present invention reflected in Table 1: HCDR2 at N61E and E62K; HCDR3 at P103V and Y105D; LCDR1 at G34Q; LCDR2 at S57D; and LCDR3 at H98L) was identified as improving the binding affinity, chemical and physical stability, and immunogenicity for monoclonal antibodies of the present invention (relative to MC-1, Jicha et al., 1997). None of the above modifications were identified in characterizations of MC-1 or the humanized MC-1 antibody constructs.

An exemplified engineered tau monoclonal antibody of the present invention is presented in Table 1. The exemplified engineered tau monoclonal antibody includes human HC framework 5-51 and human LC framework A27. The relationship of the various regions of the exemplified engineered tau monoclonal antibody is as follows (numbering of amino acids applies linear numbering; assignment of amino acids to variable domains is based on the INTERNATIONAL IMMUNOGENETICS INFORMATION SYSTEM® available at www.imgt.org; assignment of amino acids to CDR domains is based on the well-known North numbering convention, with the exception of HCDR2 which is based on the well-known Kabat numbering convention):

TABLE 1

Amino acid regions of an exemplified engineered tau monoclonal antibody of the present invention.

| | SEQ ID NO: 2 | | | SEQ ID NO: 1 | |
|---|---|---|---|---|---|
| | Region | Positions | | Region | Positions |
| HCVR | FRH1 | 1-22 | LCVR | FRL1 | 1-23 |
| | HCDR1 | 23-35 | | LCDR1 | 24-39 |
| | FRH2 | 36-49 | | FRL2 | 40-53 |
| | HCDR2 | 50-66 | | LCDR2 | 54-61 |
| | FRH3 | 67-96 | | FRL3 | 62-93 |
| | HCDR3 | 97-105 | | LCDR3 | 94-102 |
| | FRH4 | 106-116 | | FRL4 | 103-112 |
| Constant | CH | 117-442 | Constant | CL | 113-219 |

The following Examples and assays demonstrate that the monoclonal antibodies of the present invention are useful for treating neurodegenerative disorders associated with propagation of tau aggregates such as AD, PSP, or PD. It should be understood however, that the following Examples are set forth by way of illustration and not limitation, and that various modifications may be made by one of ordinary skill in the art.

EXAMPLES

Expression of Engineered Tau Antibody

Engineered tau monoclonal antibodies of the present invention can be expressed and purified essentially as follows. A glutamine synthetase (GS) expression vector containing the DNA sequence of SEQ ID NO. 11 (encoding LC amino acid sequence of SEQ ID NO. 1) and the DNA sequence of SEQ ID NO. 12 (encoding HC amino acid sequence of SEQ ID NO. 2) is used to transfect a Chinese hamster ovary cell line (CHO) by electroporation. The expression vector encodes an SV Early (Simian Virus 40E) promoter and the gene for GS. Expression of GS allows for the biochemical synthesis of glutamine, an amino acid required by the CHO cells. Post-transfection, cells undergo bulk selection with 50 µM L-methionine sulfoximine (MSX). The inhibition of GS by MSX is utilized to increase the stringency of selection. Cells with integration of the expression vector cDNA into transcriptionally active regions of the host cell genome can be selected against CHO wild type cells, which express an endogenous level of GS. Transfected pools are plated at low density to allow for close-to-clonal outgrowth of stable expressing cells. The masterwells are screened for antibody expression and then scaled up in serum-free, suspension cultures to be used for production. Clarified medium, into which the antibody has been secreted, is applied to a Protein A affinity column that has been equilibrated with a compatible buffer, such as phosphate buffered saline (pH 7.4). The column is washed with 1M NaCl to remove nonspecific binding components. The bound tau monoclonal antibody is eluted, for example, with sodium citrate at pH (approx.) 3.5 and fractions are neutralized with 1M Tris buffer. Tau monoclonal antibody fractions are detected, such as by SDS-PAGE or analytical size-exclusion, and then are pooled. Soluble aggregate and multimers may be effectively removed by common techniques, including size exclusion, hydrophobic interaction, ion exchange, or hydroxyapatite chromatography. The tau monoclonal antibody of the present invention is concentrated and/or sterile filtered using common techniques. The purity of the tau monoclonal antibody after these chromatography steps is greater than 95%. The tau monoclonal antibody of the present invention may be immediately frozen at −70° C. or stored at 4° C. for several months.

Binding Kinetics and Affinity

Surface Plasmon Resonance (SPR) assay, measured with a BIACORE® 2000 instrument (primed with HBS-EP+ running buffer (GE Healthcare, 10 mM Hepes pH7.4+150 mM NaCl+3 mM EDTA+0.05% surfactant P20) at 25° C.), is used to measure binding of exemplified tau monoclonal antibody of Example 1 to both human monomeric (e.g., native or non-aggregate) tau and human tau aggregates (both having the amino acid sequence as set forth in SEQ ID NO:13). Binding of humanized MC-1 antibody construct (having the framework combination: 5-51 heavy-chain, A27 light-chain) to human monomeric tau and human tau aggregate is measured in the same manner.

Except as noted, all reagents and materials are from BIACORE® AB (Upsala, Sweden). A CM5 chip containing immobilized protein A (generated using standard NHS-EDC amine coupling) on all four flow cells (FC) is used to employ a capture methodology. Antibody samples are prepared at 0.5 µg/mL by dilution into running buffer. Monomeric tau and fibril tau are prepared to concentrations of 2000, 1000, 500, 250, 125, 62.5, 31.25, 15.63, 7.82, 3.91, 1.95, and 0 (blank) nM by dilution into running buffer. Each analysis cycle consists of: (1) capturing antibody samples on separate flow cells (FC2, FC3, and FC4); (2) injection of 250 µL, (300 sec) of either monomeric tau or tau fibril aggregate over respective FC at a rate of 50 µL/min; (3) return to buffer flow for 20 mins. to monitor dissociation phase; (4) regeneration of chip surfaces with 25 µL (30 sec) injection of glycine, pH1.5; (5) equilibration of chip surfaces with a 50 µL (60 sec) injection of HBS-EP+.

Data of binding to tau aggregate is processed using standard double-referencing and fit to a 1:1 binding model using Biacore 2000 Evaluation software, version 4.1, to determine the association rate ($k_{on}$, $M^{-1}s^{-1}$ units), dissociation rate ($k_{off}$, $s^{-1}$ units), and $R_{max}$ (RU units). The equilibrium dissociation constant ($K_D$) was calculated from the relationship $K_D=k_{off}/k_{on}$, and is in molar units. Data of binding to monomeric tau cannot be determined accurately by SPR as described above due to rapid on- and off-rates. Therefore, $K_D$ for binding to monomeric tau is obtained by using a steady state binding fit model from plotting the concentration of antigen versus the response unit. Resulting binding data is provided in Table 2.

TABLE 2

SPR binding data to both human monomeric and aggregate tau.

| | | $k_{on}$ ($M^{-1}s^{-1}$ units) | $k_{off}$ ($M^{-1}s^{-1}$ units) | $K_D^*$ (nM) |
|---|---|---|---|---|
| Exemplified Tau mAb of Example 1 | Monomeric Tau | Not detectable | Not detectable | 235 |
| | Tau Aggregate | 4.59e4 | <1e-5 | <0.22 |
| Humanized MC-1 Ab construct | Monomeric Tau | Not determined | Not determined | 550 |
| | Tau Aggregate | 5.75e4 | 1.02e-4 | 1.77 |

*$K_D$ results are considered relative as the results are not normalized for influence of avidity.

The results provided in Table 2 demonstrate tau monoclonal antibody of Example 1 does not possess measureable binding to monomeric tau such that an affinity value can be accurately determined by Biacore analysis (due to rapid on- and off-rates). Conversely, the results provided in Table 2 demonstrate tau monoclonal antibody of Example 1 possesses improved affinity to tau aggregate compared to humanized MC-1 antibody construct.

Enzyme-Linked Immunosorbant Assay (ELISA) is used to determine relative binding affinity of the exemplified tau monoclonal antibody of Example 1 to aggregate tau fibrils from AD brain homogenates. AD brain homogenates are prepared from approx. 80 g of cortex from brain of AD patients. Briefly, buffer (TBS/1 mM PMSF/1× COMPLETE® protease inhibitor cocktail (Roche, p/n. 11 697 498 001) and phosphatase inhibitor (ThermoFischer, p/n. 78428)) is added to the AD brain tissue at about 10 ml/1 g (tissue). Tissue is homogenized using a handheld Kinematica Polytron at speed 6-7. Tissue is then further homogenized using Parr Bomb (Parr Instrument, p/n. 4653) at 1500 psi of nitrogen for 30 mins Homogenate is spun at 28,000 g (J14 Beckman rotor) for 30 min at 4° C. Supernatant is collected, pooled and run over a 4 cm high guard column of Sepharose 400 Superflow to remove larger debris, then run over 25 ml MC1-Affigel 10 column at a flow rate of 50-60 ml per hour, in order to purify MC1-binding tau fibrils. To maximize the recovery of purification, supernatants are recycled through MC-1 column over 18-20 hours at 4° C. Guard column is removed and MC1 column is washed with TBS with at least 40 column volumes. Bound tau aggregates are then eluted with 2 column volumes of 3M KSCN, collecting in approx. 1 ml fractions. Protein concentration in each eluted fraction is checked by microtiter plate Bradford assay. Fractions containing positive protein levels are pooled, concentrated to about 2 ml using Centricon (Millipore Ultracel-30K) at 4° C., and dialyzed using a Slide-A-Lyzer cassette (10K MWCO 3-12 ml, Pierce) overnight against 1 liter TBS. The concentration of tau within the tau fibrils purified from AD brain homogenate is measured by sandwich ELISA using DA-9 capture antibody and CP27 detection antibody.

Purified tau fibrils (50 µl) in PBS are coated on wells of 96-well plates (Coastar, p/n. 3690) at a concentration corresponding to 0.7 µg/ml of total tau. Plates are incubated overnight at 4° C., then washed three times with 150 µl of PBST (PBS containing 0.05% Tween-20), blocked in 100 µl BB3 (ImmunoChemistry Technology, p/n. 643) at room temperature for at least 1 hr (usually 2 hrs). Following blocking, the blocking buffer is removed from the wells. Exemplified tau monoclonal antibody of Example 1 and a humanized MC-1 antibody construct (having the framework combination: 5-51 heavy-chain, A27 light-chain) are diluted in 0.25% casein buffer to 1000 nM stock, then diluted serially 23 times with two fold dilutions. 50 µl of stock and serially diluted antibody (either exemplified tau monoclonal of Example 1 or humanized MC-1 antibody construct) are added to separate wells and incubated for 2 hours at room temperature, after which the plate is washed four times with 200 µl PBST per well. 50 µl of anti-human IgG-HRP antibodies (diluted at 1:4000 into 0.25% casein buffer) is added and incubated for 1 hour at room temperature, after which the plate is washed with 200 µl PBST per well 4 times. 50 µl of TMB/H2O2 is added and incubated at room temperature for about 10 minutes. Reaction is stopped by adding 50 µl stop solution (2N H2SO4) and colorimetric signal is measured at 450 nm Data is input into Prism 6 (GraphPad) program and $EC_{50}$ values are generated using a nonlinear regression curve fit and sigmoidal dose response. Results are presented in Table 3.

TABLE 3

$EC_{50}$ Comparison of Binding to Purified AD Tau Fibrils

| Antibody Assayed | $EC_{50}$ (pM) |
|---|---|
| exemplified tau mAb of Example 1 | 6.8 |
| humanized MC-1 Ab construct | 409.1 |

As reflected in Table 3, exemplified tau monoclonal antibody of the present invention demonstrates a 60 fold improved affinity (as measured by $EC_{50}$) to purified tau fibrils over humanized MC-1 antibody construct.

Selectivity of tau monoclonal antibody of Example 1 to tau aggregates versus tau monomer is determined by direct ELISA. Following the ELISA procedure substantially as provided above, recombinant tau (rTau) is coated on 96-well plates at a concentration corresponding to either a "high" concentration (1 µg/mL) or "low" concentration (15 ng/mL). High concentration of rTau, when coated on micro-well plates, aggregates, simulating binding to aggregated tau. Low concentration of rTau, when coated on micro-well plates, simulates binding to tau monomer. The plates, coated with high or low concentrations of rTau, respectively, are exposed to exemplified tau monoclonal antibody of Example 1 and binding of exemplified tau monoclonal antibody to the respective concentrations of rTau is measured substantially as described in the ELISA assay above. Results are provided in Table 4.

TABLE 4

$EC_{50}$ Comparison of Binding to "High" vs. "Low" Concentration of rTau

| rTau Monomer Concentration | $EC_{50}$ (pM) |
|---|---|
| "High" (1 µg/mL) | 6.0 |
| "Low" (15 ng/mL) | 722.7 |

As reflected in Table 4, exemplified tau monoclonal antibody of Example 1 demonstrates a 120 fold improved affinity (as measured by $EC_{50}$) to aggregate tau over monomeric tau.

Ex Vivo Target Engagement Studies

Binding of exemplified tau monoclonal antibody of Example 1 to aggregated tau derived from human brains is determined through immunohistochemistry staining of formalin-fixed paraffin-embedded (FFPE) brain sections obtained from: a "normal" individual (displaying minimal tau aggregation); an AD patient (displaying severe tau aggregation and NFT formation, as well as amyloid plaque pathology); a PD patient (displaying severe tau aggregation). Staining is also performed on brain sections derived from a "control" wild type mouse that possess no human tau in order to determine background non-specific staining levels.

FFPE sections are de-paraffinized and rehydrated. Thereafter, antigen retrieval (using the Lab Vision PT module system, Thermo Scientific) is performed on the sections which includes heating sections in citrate buffer (Thermo Scientific, p/n. TA-250-PM1X) for 20 minutes at 100° C. then cooling the sections in dH20. Sections are then exposed to the following seven incubation steps (at room temp.): (1) 10 min. in 0.03% H2O2; (2) 30 min in 1:20 dilution of normal goat serum (Vector Labs., p/n. S-1000) diluted in PBST; (3) 60 min. in either exemplified tau monoclonal antibody of Example 1 or humanized MC-1 antibody construct (having the framework combination: 5-51 heavy-chain, A27 light-chain) (both the exemplified tau monoclonal antibody and humanized MC-1 antibody construct are normalized to 1 mg/ml, then diluted in PBST to a dilution of 1:4000 before incubation with sections); (4) 30 min. in rabbit anti-human IgG4 (raised against the Fc region of the exemplified antibody) at a concentration of 1.1 µg/ml in PBST; (5) 30 min. in 1:200 dilution of biotinylated goat anti-rabbit IgG (Vector Labs., p/n. BA-1000) diluted in PBST: (6) 30 min. in avidin-biotin complex solution (Vector Labs., p/n. PK-7100); (7) 5 min. in 3,3'-diaminobenzidine (Vector Labs., p/n. SK-4105). Sections are washed between each of the above 7 steps using PBST. Following the seven incubation steps above, sections are counterstained with haematoxylin, dehydrated and cover-slipped. For mouse "control" tissue sections the above protocol is modified in incubation step (3) by using a 1:8000 dilution (as opposed to a 1:4000 dilution) of both the exemplified tau monoclonal antibody and humanized MC-1 antibody construct; and by replacing incubation steps (4) and (5) with a single 30 min. 1:200 dilution of biotinylated goat anti-human IgG (Vector Labs. p/n. BA-3000) in PBST.

Following procedures substantially as described above, an analysis of the binding of the exemplified tau monoclonal antibody of Example 1 to tau derived from human brains is performed. Results are provided in Table 5.

TABLE 5

Semi-quantitative analysis of binding to aggregated tau in FFPE AD brain sections.

Severity of aggregated tau detected as measured by semi quantitative scoring scheme (severe, +++; moderate, ++; mild, +; negative, −)

| | WT control (murine) | Normal control (human) | Alzheimer's disease | Pick's disease |
| --- | --- | --- | --- | --- |
| Exemplified Tau mAb of Example 1 | − | + | +++ | +++ |
| Humanized MC-1 Ab construct | − | − | + | + |

The results provided in Table 5 reflect that exemplified tau monoclonal antibody of Example 1 demonstrates significantly higher levels of staining to aggregated tau, from both AD and PD patients, in hippocampal brain sections as compared to humanized MC-1 antibody construct. The results provided in Table 5 also demonstrate that exemplified tau monoclonal antibody of Example 1 does not demonstrate higher non-specific binding than humanized MC-1 antibody construct (exemplified tau monoclonal antibody demonstrates binding to the minimal amount of aggregated tau in normal control human sections). Further, because AD and PD are characterized by distinct splicing variants of the gene encoding tau, these results support a conclusion that exemplified tau monoclonal antibody of Example 1 specifically binds the conformational epitope comprising amino acid residues 7-9 and 312-322 of human tau (residue numbering based on the exemplified human tau of SEQ ID NO. 13) common to tau aggregates of both AD and PD.

In Vitro Neutralization of Tau Aggregate Propagation

Homogenate brain preps from approx. 5 month old P301S mice are known, in the presence of native, non-aggregate tau, to induce aggregation of the native tau and to demonstrate a propagation-like effect of tau aggregation. Sarkosyl-insoluble homogenate preps of brain tissue from 4.5 to 5 month old P301S mice are sonicated and diluted with OPTI-MEM (GIBCO by Life Tech., p/n. 31985-062) to bring measured tau (per prep) to a final concentration of 0.77 µg/ml. Each prep is incubated for 30 minutes at room temperature with one of exemplified tau monoclonal antibody of Example 1 (at concentrations: 21.00, 7.00, 2.33, 0.78, 0.26, 0.09, 0.03, and 0.01 µg/ml) or humanized MC-1 antibody construct (at concentrations: 50.00, 16.67, 5.56, 1.85, 0.62, 0.21, 0.07, 0.02 and 0.01 µg/ml).

HEK293 cells (a human embryonic kidney cell line) are transfected by electroporation to inducibly express a mutant form of human tau (1N4L, which has a serine substituted for proline at residue 301 (P301S) (residue numbering based on the exemplified human tau of SEQ ID NO. 13)). (Falcon B., et al., J. Biol. Chem. 290:1049-1065, 2015). Stably transfected HEK293 cells are plated at a concentration of $1 \times 10^4$ cells/well into the wells of a 96-well plate in complete medium (D-MEM medium (Invitrogen, p/n. 11965-092), 10% fetal bovine serum (Invitrogen, p/n. 16000), 1× pen. strep (Invitrogen, p/n. 15140-122), 5 µg/ml Blasticin (Invitrogen, p/n. R210-01), 200 µg/ml Zeocin (Invitrogen, p/n. R250-01)). Plates are incubated for three days at 37° C. Following incubation, 1 mg/ml tetracycline is added at a 1:1000 dilution per well (to a final concentration of 1 µg tetracycline/ml medium) to induce expression of mutant tau. Plates are then incubated for 24 hours at 37° C. Following incubation, culture medium is removed and 50 µl of homogenate prep with one of the respective concentrations of one of exemplified tau monoclonal antibody of Example 1 or humanized MC-1 antibody construct (prepared as described above) is added. Plates are incubated for three hours, after which homogenate prep is removed and 100 µl complete medium with 1 µg/ml tetracycline and the same respective concentration of either exemplified tau monoclonal antibody or humanized MC-1 antibody construct is added to each respective well. Plates are incubated for 24 hours at 37° C., after which medium is removed and 100 µl complete medium and the same respective concentration of either exemplified tau monoclonal antibody or humanized MC-1 antibody construct is added to the respective wells. Plates are incubated for 48 hours at 37° C. Following incubation, cells are washed with 200 µl DPBS and drained.

Cells are resuspended in 50 µl H buffer (TBS pH7.4 containing 2 mM EGTA, 5 mM EDTA, protease and phosphatase inhibitor (Thermo Scientific, p/n. 784420)) per well and bath-sonicated for 10 minutes. Total protein concentration is measured by BCA™ Protein Assay (Thermo Scientific, p/n. PI-23227). Tau aggregate levels are determined by sandwich ELISA. 96-well plates are coated with 50 µl of 2

μg/ml AT8 antibody at 4° C. overnight. Plates are washed three times with PBST, then blocked with 100 μl of BB3 for 1 hour at room temperature. A standard curve is prepared using AD brain total extract by serially dilution in 0.25% casein buffer using two-fold dilutions from a starting concentration of 40 μg/ml to a final concentration of 0.3125 μg/ml. Cell lysates are diluted into 0.25% casein buffer to a total protein concentration of about 0.1 mg/ml. 50 ul of each standard sample dilution or of diluted cell samples are then added into separate wells of blocked plates and incubated at 4° C. overnight, after which plates are washed four times with PBST. Biotinylated CP27 antibody is diluted 1:2000 in 0.25% casein buffer and 50 μl is then added to into wells containing samples. Plates are incubated at room temperature for 2 hours, after which plates are washed four times with PBST. Strepavidin-HRP (Invitrogen, p/n. SNN2004) is diluted 1:5000 in 0.25% casein buffer and 50 μl is then added into each well and plates are incubated at room temperature for 1 hour. Following incubation, plates are washed 4 times with PBST and 50 μl of a 1:1 mixture of H2O2 and TMB (Thermo Scientific, p/n. 34021) is added. Plates are incubated at room temperature for 10 min. and the reaction is stopped by adding 50 μl of H2SO4. Colorimetric signal is measured at 450 nm or 650 nm AT8-positive tau levels are normalized against total protein levels in each sample. The normalized values for each sample are further normalized against AT8-positive tau levels in control samples (not treated with antibody). Percentage inhibition of tau aggregate propagation in each sample is determined by subtracting the further normalized values from 100 and the percentage of inhibition value for each sample is input into Prism 6 Software program (GraphPad) applying nonlinear regression curve fit and sigmoidal dose response for generation of $EC_{50}$ values. Results are provided in Table 6.

TABLE 6

$EC_{50}$ values representative of tau aggregate propagation inhibition.

|  | Exemplified Engineered Tau Ab of Example 1 | Humanized MC-1 Ab Construct |
|---|---|---|
| $EC_{50}$ (representing inhibition of AT8-Positive Tau Aggregate propagation (ng/mL)) | 16 | 476 |

The results provided in Table 6 reflect that exemplified tau monoclonal antibody of Example 1 demonstrates an approximately 30 fold improvement in the inhibition of induced tau aggregate propagation.

In Vivo Neutralization of Tau Aggregate Propagation

Homogenate brain stem preps from approx. 5 month old P301S mice are known to, upon injection into hippocampus of normal 10 week old female P301S mice, induce aggregation of native, non-aggregate tau, demonstrating a propagation-like effect of tau aggregation. Homogenate preps of brain stem tissue from 4.5 to 5 month old P301S mice are prepared substantially the same as described above.

Normal 10 week old female P301S mice are injected in the left hemisphere of the hippocampus with 5 μl homogenate brain prep and either: 7.5 μg exemplified tau monoclonal antibody of Example 1 (N=12); or 7.5 μg of control human IgG4 antibody (N=11). Four weeks post-injection, the mice are sacrificed and the left and right hemispheres are collected, paraffin embedded, and 6 μm serial sections are mounted on glass slides. Slides containing bregma (A-P=−2.30) are de-paraffinized, embedded tissue is rehydrated, and antigen retrieval is performed by heating slide to 100° C. for 20 min. in citrate buffer. Slides are cooled in dH2O and incubated at room temperature according to the following steps: (a) 10 min. in (0.03%) H2O2; (b) 30 min. in a 1:20 dilution of normal goat serum; (c) 60 min. in a 1:8000 dilution of PG-5 antibody (diluted in PBST)(PG-5 antibody obtained from the lab of Dr. Peter Davies, Albert Einstein College of Medicine of Yeshiva University; PG-5 antibody specifically binds serine at residue 409 of tau when phosphorylated, residue numbering based on the exemplified human tau of SEQ ID NO. 13); (d) 30 min. in a 1:200 dilution of biotinylated goat anti-mouse IgG antibody (diluted in PBST); (e) 30 min. in avidin-biotin complex solution; and (f) 5 min. in 3,3'-diaminobenzidine. PBST is used for washing between the respective steps. Following the 5 min. incubation in 3,3'-diaminobenzidine, sections are counterstained with haematoxylin, then rehydrated and coverslipped. Staining signal is measured by Scanscope AT Slide Scanner (Aperio) at 20× magnification. PG-5 immunoreactivity is quantified and expressed as a percentage using the positive pixel algorithm of Imagescope Software (v. 11.1.2.780, Aperio). Results are provided in Table 7.

TABLE 7

Mean % PG-5 immunoreactivity in left and right hippocampus, respectively.

|  | (% PG-5 Immunoreactivity) | |
|---|---|---|
|  | Left Hippocampus | Right Hippocampus |
| Exemplified Tau mAb of Example 1 | 2.52 ± 0.49 SEM | 0.63 ± 0.13 SEM |
| Control IgG4 Ab | 6.38 ± 0.93 SEM | 1.88 ± 0.31 SEM |

The results provided in Table 7 demonstrate the exemplified tau monoclonal antibody of Example 1 reduces the level of tau aggregation in both the left and right hippocampus as compared to the control IgG4 antibody. As shown, the exemplified tau monoclonal antibody produces a 60.5% greater reduction in tau aggregation in the left hippocampus, and a 66.5% greater reduction in tau aggregation in the right hippocampus, respectively, compared to control IgG4 antibody. These results demonstrate the exemplified tau monoclonal antibody possesses neutralizing activity against propagation of tau aggregation.

In Vivo Efficacy Analysis in the Tg4510 Murine Model

Transgenic Tg4510 mice express a mutant form of human tau (4R0N, which has a leucine substituted for proline at residue 301 (P301L), Ramsden M., et al., J. Neuroscience., 25: 10637-10647 (2005) and Santacruz K., et al., Science (2005); residue numbering based on the exemplified human tau of SEQ ID NO. 13). Tg4510 mice exhibit high levels of expression of the P301L mutant human tau in the hippocampus and neocortex regions, which demonstrates age-dependent tau aggregation progression.

Tau antibodies of the present invention may induce an immunogenic response in Tg4510 mice. Therefore, in order to test therapeutic potential of the tau monoclonal antibodies of the present invention for chronic administration in a rodent model, a surrogate murine tau antibody is constructed targeting the same conformational epitope and reflecting similar levels of improved affinity relative to the exemplified tau monoclonal antibody of Example 1. The surrogate tau antibody has an affinity ($EC_{50}$) to purified AD tau fibrils, measured by ELISA as described above (for exemplified tau monoclonal antibody of Example 1), to be 13.1 pM.

Eight week old female Tg4510 mice are grouped into 3 separate groups. The first group (N=15) is injected with a control mouse IgG1 antibody (15 mg/kg) twice a week for 9 weeks. The second group (N=15) is injected twice a week for 9 weeks with recombinant MC-1 antibody (15 mg/kg) produced from mouse ascites injected with MC-1 hybridoma. The third group (N=15) is injected with surrogate murine tau antibody (15 mg/kg) twice a week for 9 weeks. Following the final administration, the mice are sacrificed and their brains collected. Portions of cortex and hippocampus sections are collected, paraffin embedded, and 6 μm serial sections are mounted on glass slides for immunohistochemistry use.

Remainder of cortex region of collected brains are homogenized by pulse sonication in a volume of H buffer 10 times greater than the cortex volume, spun at 21,000 g for 20 min. at 4° C. and an aliquot of supernatant from each cortex is collected and total protein levels are determined by BCA™ Protein Assay (Thermo Scientific, p/n. PI-23227) according to manufacturer's protocol. The remainder of the supernatant is spun at 100,000 g for 1 hour at 4° C., the supernatant discarded, and the insoluble pellet obtained is resuspended in H buffer (in a volume ½ the volume of discarded supernatant). The resuspended pellet is sonicated and AT8-positive tau aggregate levels in each pellet are determined by ELISA using AT8 capture antibody and CP27 detection antibody substantially as described above. AT8-positive tau aggregate levels are normalized against total protein levels.

Similarly, remainder of hippocampus from the collected brains are homogenized by pulse sonication in a volume of H buffer 10 times greater than the hippocampus volume, spun at 21,000 g for 20 min. at 4° C., and supernatant from each hippocampus is collected and total protein levels are determined. AT8-positive tau aggregate levels in supernatant are determined by ELISA using AT8 capture antibody and CP27 detection antibody substantially as described above. AT8-positive tau aggregate levels are normalized against total protein levels. Results are provided in Table 8.

TABLE 8

Levels of AT8-positive tau aggregate in cortex and hippocampus brain homogenate measured via ELISA.

| | AT8-Positive Tau Aggregate Level (μg/mg) | |
|---|---|---|
| | Cortex | Hippocampus |
| Surrogate murine Tau Ab | 1416 ± 195 SEM | 386 ± 71 SEM |
| Control mIgG1 Ab | 1872 ± 198 SEM | 591 ± 66 SEM |
| rMC-1 mIgG1 Ab | 1703 ± 138 SEM | 510 ± 62 SEM |

The results provided in Table 8 demonstrate the surrogate murine tau antibody reduced the levels of tau aggregate in both cortex and hippocampus by 24% and 35%, respectively, relative to the control mIgG1 treated mice. The results further show mice treated with recombinant murine MC-1 antibody did not show improved reduction in levels of tau aggregate over control mIgG1 treated mice.

The level of tau aggregation in the cortex and hippocampus of the paraffin embedded sections prepared from collected brains is also measured by immunohistochemistry using PG-5 substantially as described above. Data is normalized by conversion to $\log_{10}$ values and results are summarized in Table 9.

TABLE 9

Mean $\log_{10}$ value of % PG-5 immunoreactivity in cortex and hippocampus.

| | Tau Aggregate (mean $\log_{10}$ value of % PG-5 Immunoreactivity) | |
|---|---|---|
| | Cortex | Hippocampus |
| Surrogate murine Tau Ab | 0.74 ± 0.06 | 0.26 ± 0.07 |
| Control mIgG1 Ab | 0.90 ± 0.05 | 0.46 ± 0.05 |
| rMC-1 mIgG1 Ab | 0.83 ± 0.04 | 0.34 ± 0.06 |

The results provided in Table 9 demonstrate the surrogate murine tau antibody reduces the level of tau aggregate in both the cortex (by 18%) and hippocampus (by 43%) relative to control mIgG1 antibody whereas recombinant murine MC-1 antibody did not demonstrate noticeable reduction in the level of tau aggregate in either cortex or hippocampus relative to control mIgG1 antibody.

Physical-Chemical Properties of Engineered Tau Monoclonal Antibody

The exemplified tau monoclonal antibody of Example 1 demonstrates good solubility, chemical stability, and physical stability.

Solubility:

Sufficiently high solubility is desired to enable convenient dosing. For example, a 1 mg/kg dose administered by a 1.0 mL injection into a 100 kg patient will require solubility of 100 mg/ml. In addition, maintaining the antibody in monomeric state without high molecular weight (HMW) aggregation at high concentration is also desirable. Solubility of the exemplified tau monoclonal antibody of Example 1 is analyzed by concentrating 15 mg of the exemplified antibody with a 10 K molecular weight cut-off filter (Amicon U.C. filters, Millipore, catalog # UFC903024) to a volume of less than 100 μl. The final concentration of the sample was measured by UV absorbance at A280 using a Nanodrop 2000 (Thermo Scientific).

Following procedures substantially as described above, the exemplified tau monoclonal antibody of Example 1 displays a solubility of greater than: 140 mg/ml (at pH 6 in 10 mM citrate buffer); 177 mg/ml (at pH 6 in 10 mM citrate with 150 mM NaCl); and 170 mg/ml (at pH 7.4 in PBS buffer). In addition, only low levels of HMW (from ~3 to ~5.4%) are present at high concentration and no phase separation is observed.

Chemical and Physical Stability:

Chemical stability facilitates the development of drug formulations with sufficient shelf-life. Chemical stability of the exemplified tau monoclonal antibody of Example 1 is assessed by formulating the exemplified tau antibody to a concentration of 1 mg/ml in 10 mM citrate and buffered pH 4, 5, 6, or 7. Formulated samples are incubated for four weeks at 4° C., 25° C., or 40° C. in an accelerated degradation study. Changes in charge profile of the antibody, reflecting chemical changes, are assessed using capillary isoelectric focusing (cIEF) according to standard procedures.

Following procedures substantially as described above, the exemplified tau monoclonal antibody of Example 1 demonstrates chemical stability results presented in Table 10.

TABLE 10

Summary of change in % main peak over four weeks, relative to samples incubated at 4° C., measured by cIEF and % HMW aggregates measured by SEC.

| pH | Change in % of main peak after 4 weeks (relative to 4° C.) 25° C. | Change in % HMW aggregates (relative to 4° C.) 25° C. | Change in % HMW aggregates (relative to 4° C.) 40° C. |
|---|---|---|---|
| 4 | −8.43 | −0.1 | 49.8 |
| 5 | −4.13 | 0.1 | 1.1 |
| 6 | −3.95 | −0.2 | 0.3 |
| 7 | −3.69 | −0.2 | 0.9 |

Results provided in Table 10 demonstrate that after 4 weeks storage at 40° C., the exemplified tau antibody of Example 1 has a percentage of main peak decrease of only 1.1 percentage points when formulated at pH5, and a decrease of only 0.3 percentage points when formulated at pH6 (a common pH used in antibody formulation). In addition, mass spectrometry analysis demonstrates only minimal degradation observed after 4 weeks storage at 40° C. (~1.5% LCDR1 deamidation with less than 5% degradation in all CDR sequences), indicating that the exemplified tau monoclonal antibody of Example 1 has sufficient chemical stability to facilitate development of solution formulations with adequate shelf life.

For purposes of comparison, chemical and physical stability of a humanized MC-1 antibody construct (having the framework combination: 5-51 heavy-chain, A27 light-chain) is performed by incubating the antibody for 2 weeks at 40° C. at pH8. The humanized MC-1 antibody construct showed significant chemical degradation including 12% deamidation of LCDR1, 5% deamidation and 10% isomerization in HCDR3 and 3% oxidation in HC framework.

Binding affinity, following a four week accelerated degradation study of the exemplified tau monoclonal antibody of Example 1, is assessed by formulating the exemplified monoclonal antibody to a concentration of 1 mg/ml in 10 mM citrate and buffered pH 4 or 6. Formulated samples are incubated for four weeks at 4° C. or 40° C. in an accelerated degradation study. Following incubation, binding affinity of the exemplified tau monoclonal antibody of Example 1 to rTau (15 ng/ml) coated on 96-well plates is determined by direct ELISA following the ELISA procedure substantially as described above. Results of the above-described binding affinity study, performed in duplicate, are provided in Table 11.

TABLE 11

EC$_{50}$ comparison following an accelerated degradation study.

| Formulation pH | Incubation Temp. (° C.) | EC$_{50}$ (pM) Study 1 | EC$_{50}$ (pM) Study 2 |
|---|---|---|---|
| 4 | 40 | 414 | 277 |
| 6 | 4 | 926 | 636 |
| 6 | 40 | 754 | 667 |

Table 11 demonstrates the binding affinity of the exemplified tau monoclonal antibody of Example 1 to low concentrations of rTau remained similar for samples following a four week accelerated degradation, as compared to control samples incubated at 4° C.

Sequences

SEQ ID NO: 1 - LC of exemplified tau monoclonal antibody of Example 1
EIVLTQSPGTLSLSPGERATLSCRSSQSLVHSNQNTYLHWYQQKPGQAPR
LLIYKVDNRFSGIPDRFSGSGSGTDFTLTISRLEPEDFAVYYCSQSTLVP
LTFGGGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC SEQ ID NO: 2 - HC of exemplified tau monoclonal antibody of Example 1
EVQLVQSGAEVKKPGESLKISCKGSGYTFSNYWIEWVRQMPGKGLEWMGE
ILPGSDSIKYEKNFKGQVTISADKSISTAYLQWSSLKASDTAMYYCARRG
NYVDDWGQGTLVTVSSASTKGPSVFPLAPCSRSTSESTAALGCLVKDYFP
EPVTVSWNSGALTSGVHTFPAVLQSSGLYSLSSVVIVPSSSLGTKTYTCN
VDHKPSNTKVDKRVESKYGPPCPPCPAPEAAGGPSVFLFPPKPKDTLMIS
RTPEVTCVVVDVSQEDPEVQFNWYVDGVEVHNAKTKPREEQFNSTYRVVS
VLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSF
FLYSRLTVDKSRWQEGNVFSCSVMHEALHNHYTQKSLSLSLG SEQ ID NO: 3 - LCDR1 of exemplified tau monoclonal antibody of Example 1
RSSQSLVHSNQNTYLH SEQ ID NO: 4 - LCDR2 of exemplified tau monoclonal antibody of Example 1
YKVDNRFS SEQ ID NO: 5 - LCDR3 of exemplified tau monoclonal antibody of Example 1
SQSTLVPLT SEQ ID NO: 6 - HCDR1 of exemplified tau monoclonal antibody of Example 1
KGSGYTFSNYWIE SEQ ID NO: 7 - HCDR2 of exemplified tau monoclonal antibody of Example 1
EILPGSDSIKYEKNFKG SEQ ID NO: 8 - HCDR3 of exemplified tau monoclonal antibody of Example 1
ARRGNYVDD SEQ ID NO: 9 - LCVR of exemplified tau monoclonal antibody of Example 1
EIVLTQSPGTLSLSPGERATLSCRSSQSLVHSNQNTYLHWYQQKPGQAPR
LLIYKVDNRFSGIPDRFSGSGSGTDFTLTISRLEPEDFAVYYCSQSTLVP
LTFGGGTKVEIK SEQ ID NO: 10 - HCVR of exemplified tau monoclonal antibody of Example 1
EVQLVQSGAEVKKPGESLKISCKGSGYTFSNYWIEWVRQMPGKGLEWMGE
ILPGSDSIKYEKNFKGQVTISADKSISTAYLQWSSLKASDTAMYYCARRG
NYVDDWGQGTLVTVSS SEQ ID NO: 11 - Nucleotide Sequence Encoding the Exemplified LC (SEQ ID NO: 1)
gaaattgtgttgacgcagtctccaggcaccctgtctttgtctcagggga
aagagccaccctctcctgcagatctagtcagagccttgtacacagtaatc
agaacacctatttacattggtaccagcagaaacctggccaggctcccagg
ctcctcatctataaagttgacaacctatttctggcatcccagacaggtt
cagtggcagtgggtctgggacagacttcactctcaccatcagcagactgg
agcctgaagattttgcagtgtattactgttctcaaagtacactggttccg
ctcacgttcggcggagggaccaaggtggagatcaaacgaccgtggctgc
accatctgtcttcatcttcccgccatctgatgagcagttgaaatctgaga
ctgcctctgttgtgtgcctgctgaataacttctatcccagagaggccaaa
gtacagtggaaggtggataacgcctccaatcgggtaactcccaggagag
tgtcacagagcaggacagcaaggacagcacctacagcctcagcagcaccc
tgacgctgagcaaagcagactacgagaaacacaaagtctacgcctgcgaa
gtcacccatcagggcctgagctcgcccgtcacaaagagcttcaacagggg
agagtgc SEQ ID NO: 12 - Nucleotide Sequence Encoding the Exemplified HC (SEQ ID NO: 2)
gaggtgcagctggtgcagtctggagcagaggtgaaaaagcccggggagtc
tctgaagatctcctgtaagggttctggctacacattcagtaactactgga
tagagtgggtgcgccagatgcccgggaaaggcctggagtggatgggggag
attttacctggaagtgatagtattaagtacgaaaagaatttcaagggcca

Sequences

```
ggtcaccatctcagccgacaagtccatcagcaccgcctacctgcagtgga
gcagcctgaaggcctcggacaccgccatgtattactgtgcgagaagggg
aactacgtggacgactggggccagggcaccctggtcaccgtctcctcagc
ttctaccaagggcccatccggtcttccccgctagcgccctgctccaggagca
cctccgagagcacagccgccctgggctgcctggtcaaggactacttccc
gaaccggtgacggtgtcgtggaactcaggcgccctgaccagcggcgtgca
caccttcccggctgtcctacagtcctcaggactctactccctcagcagcg
tggtgaccgtgccctccagcagcttgggcacgaagacctacacctgcaac
gtagatcacaagcccagcaacaccaaggtggacaagagagttgagtccaa
atatggtccccatgcccaccctgcccagcacctgaggccgccggggac
catcagtcttcctgttccccccaaaacccaaggacactctcatgatctcc
cggaccccctgaggtcacgtgcgtggtggtggacgtgagccaggaagaccc
cgaggtccagttcaactggtacgtggatggcgtggaggtgcataatgcca
agacaaagccgcgggaggagcagttcaacagcacgtaccgtgtggtcagc
gtcctcaccgtcctgcaccaggactggctgaacggcaaggagtacaagtg
caaggtctccaacaaaggcctcccgtcctcatcgagaaaaccatctcca
aagccaaagggcagccccgagagccacaggtgtacaccctgcccccatcc
caggaggagatgaccaagaaccaggtcagcctgacctgcctggtcaaagg
```

Sequences

```
cttctaccccagcgacatcgccgtggagtgggaaagcaatgggcagccgg
agaacaactacaagaccacgcctcccgtgctggactccgacggctccttc
ttcctctacagcaggctaaccgtggacaagagcaggtggcaggagggga
atgtcttctcatgctccgtgatgcatgaggctctgcacaaccactacacac
agaagagcctctccctgtctctgggt
```

SEQ ID NO: 13 - Amino Acid Sequence of Human, Full-Length Tau

```
MAEPRQEFEVMEDHAGTYGLGDRKDQGGYTMHQDQEGDTDAGLKESPLQT
PTEDGSEEPGSETSDAKSTPTAEDVTAPLVDEGAPGKQAAAQPHTEIPEG
TTAEEAGIGDTPSLEDEAAGHVTQARMVSKSKDGTGSDDKKAKGADGKTK
IATPRGAAPPGQKGQANATRIPAKTPPAPKTPPSSGEPPKSGDRSGYSSP
GSPGTPGSRSRTPSLPTPPTREPKKVAVVRTPPKSPSSAKSRLQTAPVPM
PDLKNVKSKIGSTENLKHQPGGGKVQIINKKLDLSNVQSKCGSKDNIKHV
PGGGSVQIVYKPVDLSKVTSKCGSLGNIHHKPGGGQVEVKSEKLDFKDRV
QSKIGSLDNITHVPGGGNKKIETHKLTFRENAKAKTDHGAEIVYKSPVVS
GDTSPRHLSNVSSTGSIDMVDSPQLATLADEVSASLAKQGL
```

We claim:

1. A method of treating Alzheimer's disease, Progressive Supranuclear Palsy or Pick's disease comprising administering to a patient in need thereof an effective amount of a monoclonal antibody that binds human tau, wherein said monoclonal antibody comprises a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2, and HCDR3, wherein the amino acid sequence of LCDR1 is set forth by SEQ ID NO: 3, the amino acid sequence of LCDR2 is set forth by SEQ ID NO: 4, the amino acid sequence of LCDR3 is set forth by SEQ ID NO: 5, the amino acid sequence of HCDR1 is set forth by SEQ ID NO: 6, the amino acid sequence of HCDR2 is set forth by SEQ ID NO: 7, and the amino acid sequence of HCDR3 is set forth by SEQ ID NO: 8.

2. The method of claim 1, wherein the monoclonal antibody comprises a light chain variable region (LCVR) and a heavy chain variable region (HCVR), wherein the amino acid sequence of the LCVR is set forth by SEQ ID NO: 9 and the amino acid sequence of the HCVR is set forth by SEQ ID NO: 10.

3. The method of claim 1, wherein the monoclonal antibody comprises a light chain (LC) and a heavy chain (HC), wherein the amino acid sequence of the LC is set forth by SEQ ID NO: 1 and the amino acid sequence of the HC is set forth by SEQ ID NO: 2.

4. A method of treating Alzheimer's disease, Progressive Supranuclear Palsy or Pick's disease comprising administering to a patient in need thereof a pharmaceutical composition comprising a monoclonal antibody that binds human tau, wherein said monoclonal antibody comprises a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2, and HCDR3, wherein the amino acid sequence of LCDR1 is set forth by SEQ ID NO: 3, the amino acid sequence of LCDR2 is set forth by SEQ ID NO: 4, the amino acid sequence of LCDR3 is set forth by SEQ ID NO: 5, the amino acid sequence of HCDR1 is set forth by SEQ ID NO: 6, the amino acid sequence of HCDR2 is set forth by SEQ ID NO: 7, and the amino acid sequence of HCDR3 is set forth by SEQ ID NO: 8, and one or more pharmaceutically acceptable carriers, diluents or excipients.

5. The method of claim 4, wherein the pharmaceutical composition comprises a monoclonal antibody comprising a light chain variable region (LCVR) and a heavy chain variable region (HCVR), wherein the amino acid sequence of the LCVR is set forth by SEQ ID NO: 9 and the amino acid sequence of the HCVR is set forth by SEQ ID NO: 10.

6. The method of claim 4, wherein the pharmaceutical composition comprises a monoclonal antibody comprising a light chain (LC) and a heavy chain (HC), wherein the amino acid sequence of the LC is set forth by SEQ ID NO: 1 and the amino acid sequence of the HC is set forth by SEQ ID NO: 2.

* * * * *

SEQUENCE LISTING

<160> NUMBER OF SEQ ID NOS: 13

<210> SEQ ID NO 1
<211> LENGTH: 219
<212> TYPE: PRT
<213> ORGANISM: Artificial Sequence
<220> FEATURE:
<223> OTHER INFORMATION: LC of exemplified tau monoclonal antibody of Example 1

<400> SEQUENCE: 1

```
Glu Ile Val Leu Thr Gln Ser Pro Gly Thr Leu Ser Leu Ser Pro Gly
1               5                   10                  15

Glu Arg Ala Thr Leu Ser Cys Arg Ser Gln Ser Leu Val His Ser
            20                  25                  30

Asn Gln Asn Thr Tyr Leu His Trp Tyr Gln Gln Lys Pro Gly Gln Ala
        35                  40                  45

Pro Arg Leu Leu Ile Tyr Lys Val Asp Asn Arg Phe Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ser Gln Ser
                85                  90                  95

Thr Leu Val Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 2
<211> LENGTH: 442
<212> TYPE: PRT
<213> ORGANISM: Artificial Sequence
<220> FEATURE:
<223> OTHER INFORMATION: HC of exemplified tau monoclonal antibody of Example 1

<400> SEQUENCE: 2

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Ser Asn Tyr
            20                  25                  30

Trp Ile Glu Trp Val Arg Gln Met Pro Gly Lys Gly Leu Glu Trp Met
        35                  40                  45

Gly Glu Ile Leu Pro Gly Ser Asp Ser Ile Lys Tyr Glu Lys Asn Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly Asn Tyr Val Asp Asp Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
```

```
                355                 360                 365
Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 3
<211> LENGTH: 16
<212> TYPE: PRT
<213> ORGANISM: Artificial Sequence
<220> FEATURE:
<223> OTHER INFORMATION: LCDR1 of exemplified tau monoclonal antibody of
      Example 1

<400> SEQUENCE: 3

Arg Ser Ser Gln Ser Leu Val His Ser Asn Gln Asn Thr Tyr Leu His
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: LCDR2 of exemplified tau monoclonal antibody of
      Example 1

<400> SEQUENCE: 4

Tyr Lys Val Asp Asn Arg Phe Ser
1               5

<210> SEQ ID NO 5
<211> LENGTH: 9
<212> TYPE: PRT
<213> ORGANISM: Artificial Sequence
<220> FEATURE:
<223> OTHER INFORMATION: LCDR3 of exemplified tau monoclonal antibody of
      Example 1

<400> SEQUENCE: 5

Ser Gln Ser Thr Leu Val Pro Leu Thr
1               5

<210> SEQ ID NO 6
<211> LENGTH: 13
<212> TYPE: PRT
<213> ORGANISM: Artificial Sequence
<220> FEATURE:
<223> OTHER INFORMATION: HCDR1 of exemplified tau monoclonal antibody of
      Example 1

<400> SEQUENCE: 6

Lys Gly Ser Gly Tyr Thr Phe Ser Asn Tyr Trp Ile Glu
1               5                   10

<210> SEQ ID NO 7
<211> LENGTH: 17
<212> TYPE: PRT
<213> ORGANISM: Artificial Sequence
<220> FEATURE:
```

-continued

<223> OTHER INFORMATION: HCDR2 of exemplified tau monoclonal antibody of
    Example 1

<400> SEQUENCE: 7

Glu Ile Leu Pro Gly Ser Asp Ser Ile Lys Tyr Glu Lys Asn Phe Lys
1               5                   10                  15
Gly

<210> SEQ ID NO 8
<211> LENGTH: 9
<212> TYPE: PRT
<213> ORGANISM: Artificial Sequence
<220> FEATURE:
<223> OTHER INFORMATION: HCDR3 of exemplified tau monoclonal antibody of
    Example 1

<400> SEQUENCE: 8

Ala Arg Arg Gly Asn Tyr Val Asp Asp
1               5

<210> SEQ ID NO 9
<211> LENGTH: 112
<212> TYPE: PRT
<213> ORGANISM: Artificial Sequence
<220> FEATURE:
<223> OTHER INFORMATION: LCVR of exemplified tau monoclonal antibody of
    Example 1

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ser Gln Ser Leu Val His Ser
            20                  25                  30

Asn Gln Asn Thr Tyr Leu His Trp Tyr Gln Gln Lys Pro Gly Gln Ala
        35                  40                  45

Pro Arg Leu Leu Ile Tyr Lys Val Asp Asn Arg Phe Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ser Gln Ser
                85                  90                  95

Thr Leu Val Pro Leu Thr Phe Gly Gly Gly Thr Lys Val Glu Ile Lys
            100                 105                 110

<210> SEQ ID NO 10
<211> LENGTH: 116
<212> TYPE: PRT
<213> ORGANISM: Artificial Sequence
<220> FEATURE:
<223> OTHER INFORMATION: HCVR of exemplified tau monoclonal antibody of
    Example 1

<400> SEQUENCE: 10

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Ser Asn Tyr
            20                  25                  30

Trp Ile Glu Trp Val Arg Gln Met Pro Gly Lys Gly Leu Glu Trp Met
        35                  40                  45

Gly Glu Ile Leu Pro Gly Ser Asp Ser Ile Lys Tyr Glu Lys Asn Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Gly Asn Tyr Val Asp Asp Trp Gly Gln Gly Thr Leu Val
            100                 105                 110

Thr Val Ser Ser
        115

<210> SEQ ID NO 11
<211> LENGTH: 657
<212> TYPE: DNA
<213> ORGANISM: Artificial Sequence
<220> FEATURE:
<223> OTHER INFORMATION: Nucleotide Sequence Encoding the Exemplified
      LC (SEQ ID NO:1)

<400> SEQUENCE: 11
gaaattgtgt tgacgcagtc tccaggcacc ctgtctttgt ctccagggga aagagccacc        60
ctctcctgca gatctagtca gagccttgta cacagtaatc agaacaccta tttacattgg      120
taccagcaga aacctggcca ggctcccagg ctcctcatct ataaagttga caaccgattt      180
tctggcatcc cagacaggtt cagtggcagt gggtctggga cagacttcac tctcaccatc      240
agcagactgg agcctgaaga ttttgcagtg tattactgtt ctcaaagtac actggttccg      300
ctcacgttcg gcggagggac caaggtggag atcaaacgga ccgtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgc        657

<210> SEQ ID NO 12
<211> LENGTH: 1326
<212> TYPE: DNA
<213> ORGANISM: Artificial Sequence
<220> FEATURE:
<223> OTHER INFORMATION: Nucleotide Sequence Encoding the Exemplified
      HC (SEQ ID NO: 2)

<400> SEQUENCE: 12
gaggtgcagc tggtgcagtc tggagcagag gtgaaaaagc ccggggagtc tctgaagatc        60
tcctgtaagg gttctggcta cacattcagt aactactgga tagagtgggt gcgccagatg      120
cccgggaaag gcctggagtg gatgggggag attttacctg gaagtgatag tattaagtac      180
gaaaagaatt tcaagggcca ggtcaccatc tcagccgaca gtccatcag caccgcctac      240 ctgcagtgga gcagcctgaa ggcctcggac accgccatgt attactgtgc gagaaggggg      300
aactacgtgg acgactgggg ccagggcacc ctggtcaccg tctcctcagc ttctaccaag      360
ggcccatcgg tcttccccgct agcgccctgc tccaggagca cctccgagag cacagccgcc      420
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgaccgt gccctccagc agcttgggca cgaagaccta cacctgcaac      600
gtagatcaca agcccagcaa caccaaggtg gacaagagag ttgagtccaa atatggtccc      660
ccatgcccac cctgcccagc acctgaggcc gccgggggac catcagtctt cctgttcccc      720

```
ccaaaaccca aggacactct catgatctcc cggaccctg aggtcacgtg cgtggtggtg      780
gacgtgagcc aggaagaccc cgaggtccag ttcaactggt acgtggatgg cgtggaggtg      840
cataatgcca agacaaagcc gcgggaggag cagttcaaca gcacgtaccg tgtggtcagc      900
gtcctcaccg tcctgcacca ggactggctg aacggcaagg agtacaagtg caaggtctcc      960
aacaaaggcc tcccgtcctc catcgagaaa accatctcca aagccaaagg gcagcccga     1020 gagccacagg tgtacaccct gccccatcc caggaggaga tgaccaagaa ccaggtcagc     1080
ctgacctgcc tggtcaaagg cttctacccc agcgacatcg ccgtggagtg ggaaagcaat     1140
gggcagccgg agaacaacta caagaccacg cctcccgtgc tggactccga cggctccttc     1200
ttcctctaca gcaggctaac cgtggacaag agcaggtggc aggaggggaa tgtcttctca     1260
tgctccgtga tgcatgaggc tctgcacaac cactacacac agaagagcct ctccctgtct     1320
ctgggt                                                               1326
```

<210> SEQ ID NO 13
<211> LENGTH: 441
<212> TYPE: PRT
<213> ORGANISM: Artificial Sequence
<220> FEATURE:
<223> OTHER INFORMATION: Amino Acid Sequence of Human, Full-Length Tau

<400> SEQUENCE: 13

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
```

-continued

```
                    245                 250                 255
Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440
```